United States Patent [19]
von Windheim et al.

[11] Patent Number: 5,285,084
[45] Date of Patent: Feb. 8, 1994

[54] DIAMOND SCHOTTKY DIODES AND GAS SENSORS FABRICATED THEREFROM

[75] Inventors: Jesko von Windheim; Vasudev Venkatesan, both of Raleigh, N.C.

[73] Assignee: Kobe Steel USA, Research Triangle Park, N.C.

[21] Appl. No.: 939,446

[22] Filed: Sep. 2, 1992

[51] Int. Cl.$^5$ ............................................. H01L 29/66
[52] U.S. Cl. ..................................... 257/77; 257/414; 257/485; 257/475; 204/431; 204/432; 204/424; 204/419
[58] Field of Search ............... 204/416, 419, 431, 432, 204/424, 426; 257/414, 77, 76, 485, 471, 453, 486, 475

[56] References Cited

U.S. PATENT DOCUMENTS

| | | | |
|---|---|---|---|
| 4,982,243 | 1/1991 | Nakahata et al. | 257/77 |
| 5,002,899 | 3/1991 | Geis et al. | 257/77 X |
| 5,086,014 | 2/1992 | Miyata et al. | 257/77 X |
| 5,132,749 | 7/1992 | Nishibayashi et al. | 257/471 X |
| 5,144,380 | 9/1992 | Kimoto et al. | 257/77 |
| 5,173,761 | 12/1992 | Dreifus et al. | 257/77 X |

FOREIGN PATENT DOCUMENTS

0457508 11/1991 European Pat. Off. ............... 257/77

OTHER PUBLICATIONS

Miyata et al., "Metal-Intrinsic Semiconductor-Semiconductor Structures Using Polycrystalline Diamond Films" *Appl. Phys. Lett.*, vol. 60, No. 4, Jun. 1992, pp. 480-482.
Fountain et al., "Effect of Thin Interfacial SiO$_2$ Films on Metal Contacts to B-Doped Diamond Films," *J. Electrochem. Soc.*, vol. 139, No. 5, May 1992, pp. 1445-1449.
Glover, "The C-V Characteristics of Schottky Barriers on Laboratory Grown Semiconducting Diamonds," *Solid-State Electronics*, vol. 16, 1973, pp. 973-983.
"A Thermally Activated Solid State Reaction Process for Fabricating Ohmic Contacts to Semiconducting Diamond," *J. Appl. Physics*, 68(5), Sep. 1990, pp. 2246-2254, Moazed et al.
Use of Electroreflectance Technique in Pt/GaAs Schottky Barrier Sensor Characterization, Lechuga et al., Sensors and Actuators, vol. 32, pp. 354-356, 1992.
The C-V Characteristics of Schottky Barriers on Laboratory Grown Semiconducting Diamonds, G. H. Glover, Solid State Electronics, vol. 16, pp. 973-983, 1973.
Electrical Characteristics of Schottky Diodes Fabricated Using Plasma Assisted Chemical Vapor Deposited Diamond Films, Gildenblat et al., Appl. Phys. Lett. vol. 53, No. 7, pp. 586-588, 1986.
A Thermally Activated Solid State Reaction Process for Fabricating Ohmic Contacts to Semiconducting Diamond, Moazed et al., J. Appl. Phys., vol. 68, No. 5, pp. 2246-2254, 1990.
Metal-Intrinsic Semiconductor-Semiconductor Structures Using Polycrystalline Diamond Films, Miyata et al., Appl. Phys. Letter., vol. 60, No. 4, pp. 480-482, 1992, Jun.
Effect of Thin Interfacial SiO$_2$ Films on Metal Contacts to B-Doped Diamond Films, Fountain et al., J. Electrochem. Soc., vol. 139, No. 5, pp. 1445-1449, May, 1992.
Capacitance-Voltage Measurements on Metal-SiO$_2$ Diamond Structures Fabricated with (100)-and (111)-Oriented Substrates, Geis et al., IEEE Transactions on Electron Devices, vol. 38, No. 3, pp. 619-626, 1991.

*Primary Examiner*—William Mintel
*Attorney, Agent, or Firm*—Bell, Seltzer, Park & Gibson

[57] ABSTRACT

Schottky diodes and gas sensors include a diamond layer having a Schottky contact thereon and an ohmic contact thereon, wherein the diamond layer includes a highly doped region adjacent the ohmic contact to provide a low resistance ohmic contact. Dramatically reduced frequency dependence of the capacitance/voltage characteristic of Schottky diodes and gas sensors formed thereby, compared to Schottky diodes and gas sensors which do not include the highly doped region adjacent the ohmic contact, is provided. The highly doped region is preferably boron doped at a concentration of at least $10^{20}$ atoms per cubic centimeter to form an ohmic contact with a contact resistance of less than $10^{-3}$ $\Omega$-cm$^2$. The ohmic contact is preferably a back contact on the face of the diamond layer opposite the Schottky contact.

26 Claims, 6 Drawing Sheets

DIAMOND SCHOTTKY DIODES AND GAS SENSORS FABRICATED THEREFROM

FIELD OF THE INVENTION

This invention relates to microelectronic devices, and more particularly to microelectronic devices fabricated of diamond.

BACKGROUND OF THE INVENTION

Schottky diodes are widely used microelectronic devices. As is well known to those having skill in the art, a diode exhibits a very low resistance to current flow in one direction and a very high resistance to current flow in the opposite direction, thereby producing current rectification. As is also well known to those having skill in the art, a Schottky diode produces rectification as a result of nonlinear current transport across a metal-semiconductor contact.

Schottky diodes are also widely used as gas sensors. For example, a Schottky diode using a catalytic metal contact such as platinum or palladium, has been shown to be an excellent hydrogen gas sensor. In a Schottky diode, the Schottky barrier height decreases when the device is exposed to a hydrogen containing atmosphere. The hydrogen induced changes are typically detected as a modification of the capacitance voltage (C-V) or the current voltage (I-V) characteristics of the diode. See, for example, a publication entitled Use of the Electroreflectance Technique in Pt/GaAs Schottky Barrier Sensor Characterization by Lechuga et al., Sensors and Actuators, Vol. 32, pp. 354-356, 1992.

Diamond is a preferred material for semiconductor devices because it has semiconductor properties that are better than silicon, germanium or gallium arsenide. Diamond provides a higher energy bandgap, a higher breakdown voltage and a higher saturation velocity than these traditional semiconductor materials.

These properties of diamond yield a substantial increase in projected cutoff frequency and maximum operating voltage compared to devices fabricated using silicon, germanium or gallium arsenide. Silicon is typically not used at temperatures higher than about 200° C. and gallium arsenide is not typically used above 300° C. These temperature limitations are caused, in part, because of the relatively small energy band gaps for silicon (1.12 eV at ambient temperature) and gallium arsenide (1.42 Ev at ambient temperature). Diamond, in contrast, has a large band gap of 5.47 Ev at ambient temperature, and is thermally stable up to about 1400° C.

Diamond has the highest thermal conductivity of any solid at room temperature and exhibits good thermal conductivity over a wide temperature range. The high thermal conductivity of diamond may be advantageously used to remove waste heat from an integrated circuit, particularly as integration densities increase. In addition, diamond has a smaller neutron cross-section which reduces its degradation in radioactive environments, i.e., diamond is a "radiation-hard" material.

Because of the advantages of diamond as a material for semiconductor devices, there is at present an interest in the growth and use of diamond for Schottky diodes and Schottky diode gas sensors. Unfortunately, it has been found that Schottky diodes fabricated from diamond exhibit frequency dependence of their capacitance/voltage characteristic, thereby limiting the usefulness of diamond based Schottky diodes and gas sensors.

The frequency dependent variation of the capacitance/voltage characteristic of diamond based Schottky devices has been widely investigated. See, for example, the publications entitled The C-V Characteristics of Schottky Barriers on Laboratory Grown Semiconducting Diamonds by Glover, Solid State Electronics, Vol. 16, pp. 973-983 (1973); and Electrical Characteristics of Schottky Diodes Fabricated Using Plasma Assisted Chemical Vapor Deposited Diamond Films by Gildenblat et al., Applied Physics Letters, Vol. 53, No. 7, pp. 586-588 (1986).

In these investigations, the frequency dependent variation in capacitance/voltage characteristic has been attributed to the presence of deep level states in the diamond band gap, and to the high resistivity of bulk diamond as a result of diamond's unique energy level structure. Accordingly, characterizations of Schottky contacts have heretofore assumed that the undesirable frequency dependence of the capacitance/voltage characteristic was as a result of the inherent energy level structure (i.e. the deep level states in the diamond bandgap) and high series resistance of the diamond material itself. This undesirable frequency dependence limits the usefulness of diamond based Schottky diodes and gas sensors, notwithstanding the advantages of diamond as a material for semiconductor devices, especially in high frequency or fast transient applications.

SUMMARY OF THE INVENTION

It is therefore an object of the invention to provide a diamond Schottky diode.

It is another object of the present invention to provide a gas sensor using a diamond Schottky diode.

It is yet another object of the invention to provide a diamond Schottky diode and gas sensor fabricated therefrom, which exhibit reduced frequency dependence of their capacitance/voltage characteristic.

These and other objects are provided, according to the present invention, by a Schottky diode and gas sensor which includes a diamond layer having a Schottky contact thereon and an ohmic contact thereon, wherein the diamond layer includes a highly doped region adjacent the ohmic contact to provide a low resistance ohmic contact. It has been found, according to the invention, that the frequency dependence of the capacitance/voltage characteristic of Schottky diodes and gas sensors formed thereby is not primarily related to the presence of deep level states in the diamond band gap, as has been assumed for a period of over twenty years. Rather, according to the invention, it has been found that the strong frequency dependence is primarily as a result of the high impedance (i.e. resistance and capacitance) of the "ohmic" contact which is typically applied to the diamond layer. The high series resistance of diamond also plays an important role in the frequency dependence, as has already been known. When the diamond layer includes a highly doped region adjacent the ohmic contact, the frequency dependence of the capacitance/voltage characteristic is reduced significantly. Schottky diodes and gas sensors with improved operational characteristics are thereby provided.

According to the invention, the highly doped region adjacent the ohmic contact is preferably boron doped at a concentration of at least $10^{20}$ cm$^{-3}$. This doping forms an ohmic contact with a contact resistance of less than $10^{-3}$ $\Omega$-cm$^2$. Preferably, the ohmic contact is a back contact on a face of a diamond layer opposite a Schottky contact.

The diamond layer of the present invention can be a monocrystalline diamond layer or a polycrystalline diamond layer. The diamond layer may itself be formed on a diamond or a nondiamond substrate using techniques well known to those having skill in the art. When a back ohmic contact is formed on the diamond layer, a portion of the substrate is preferably removed to expose the back face of the diamond layer, opposite the Schottky contact, and allow the highly doped boron region to be formed. A metal contact is formed on the boron doped region.

The highly doped boron region can be formed in the diamond layer by in situ boron doping or boron ion implantation using techniques well known to those having skill in the art. By providing a highly doped boron layer adjacent the ohmic contact to the Schottky diode or gas sensor, frequency variations of the capacitance/voltage characteristics are reduced.

A gas sensor according to the invention includes a diamond layer having first and second opposing faces, and a first contact on the first face, wherein the first contact forms a Schottky barrier of predetermined Schottky barrier height between the first contact and the first face. The first contact allows gas to interact with the first face, to thereby alter the predetermined Schottky barrier height. The contact is preferably a catalytic metal contact such as platinum or palladium, which is sufficiently thin to allow gas to interact with the diamond layer. Preferably the catalytic metal layer is less than 1000 Å thick. When the diamond layer is a layer of polycrystalline diamond, a layer of undoped diamond or a thin layer of silicon dioxide is also preferably included between the metal layer and the polycrystalline diamond layer. The gas sensor also includes a second contact, preferably on the second face, and the diamond layer includes a highly doped region, preferably boron doped at a concentration of at least $10^{20}$ cm$^{-3}$, adjacent the second contact, to form an ohmic contact having a contact resistance of less than $10^{-3}$ $\Omega$cm$^2$. An improved gas sensor is thereby provided.

DESCRIPTION OF A PREFERRED EMBODIMENT

Figure 1:
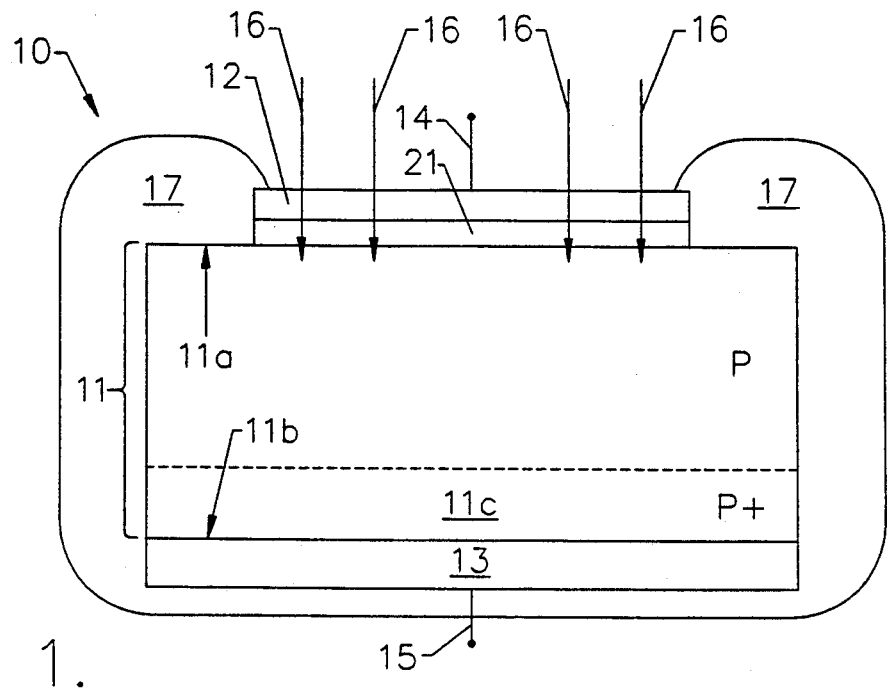
FIG. 1 illustrates a cross-sectional view of a first embodiment of a gas sensor according to the present invention.

The present invention now will be described more fully hereinafter with reference to the accompanying drawings, in which a preferred embodiment of the invention is shown. This invention may, however, be embodied in many different forms and should not be construed as limited to the embodiment set forth herein; rather, this embodiment is provided so that this disclosure will be thorough and complete, and will fully convey the scope of the invention to those skilled in the art. In the drawings, the thickness of layers and regions and positions of grain boundaries are exaggerated for clarity. Like numbers refer to like elements throughout.

Referring now to FIG. 1, a first embodiment of a diamond gas sensor according to the present invention is shown. Gas sensor 10 includes a diamond layer 11, preferably between about 1 $\mu$m and about 250 $\mu$m thick, and which is lightly doped, preferably at a boron concentration of $10^{15}$–$10^{18}$ atoms cm$^{-3}$. Diamond layer 11 may be a monocrystalline diamond layer or a polycrystalline diamond layer and may be formed using techniques well known to those having skill in the art. Diamond layer 11 includes a first face 11a and a second face 11b. Other high bulk resistance semiconductors, such as silicon carbide or gallium nitride may be used.

As also shown in FIG. 1, diamond layer 11 includes a highly doped region 11c at second face 11b. Layer 11c is preferably between about 0.3 $\mu$m and about 1 $\mu$m thick and is heavily doped with boron at $10^{20}$–$10^{21}$ atoms cm$^{-3}$ to produce a P++ region.

Still referring to FIG. 1, a Schottky contact 12 is formed on first face 11a of diamond layer 11. Schottky contact 12 is formed of a metal which forms a Schottky barrier with diamond. Schottky contact 12 is preferably formed of a catalytic metal such as platinum or palladium. The catalytic metal allows the sensing gas to rapidly pass therethrough in a direction shown by arrows 16 and interact with the first face 11a of diamond layer 11. Schottky contact 12 is preferably sufficiently thin to allow the gas to interact with the diamond layer. When platinum or palladium is used, a thickness of less than about 1000 Å is preferred.

As described above, diamond layer 11 may be a monocrystalline diamond layer or a polycrystalline diamond layer. When a monocrystalline diamond layer is used, the Schottky contact 12 is typically formed directly on the first face 11a of monocrystalline diamond layer 11. However, when a polycrystalline diamond layer is used, a Schottky contact is preferably formed by including an intermediate layer 21 between the metal 12 and the polycrystalline diamond layer 11. This intermediate layer is preferably a layer of undoped (insulating) diamond, about 2000 Å thick, as described in the publication by Miyata et al. entitled Metal-Intrinsic Semiconductor-Semiconductor Structures Using Polycrystalline Diamond Films, Applied Physics Letters, Vol. 60, No. 4 (1992), pp. 480–482. Alternatively, intermediate layer 21 may be a very thin layer of silicon dioxide (SiO$_2$), about 20 Å thick, between metal layer 12 and polycrystalline diamond layer 11, as described in a publication by coinventor V. Venkatesan et al. entitled Effect of Thin Interfacial SiO$_2$ Films on Metal Contacts to B-Doped Diamond Films, Journal of the Electrochemical Society, Vol. 139, No. 5 (1992), pp. 1445-1449.

As is well known to those having skill in the art, the gas which enters substrate 11, as shown by arrows 16, alters the barrier height of the Schottky barrier formed between contact 12 and face 11a. This change in barrier height is used as a criteria for detecting the gas, using techniques well known to those having skill in the art. Heretofore, the frequency dependence of the capacitance of the Schottky contact was a strong influence in the determination of barrier height. It was thought that this frequency dependence was due to the presence of deep level states in the diamond band gap and to the high resistivity of the diamond layer 11. Accordingly, the inherent characteristics of diamond itself were heretofore thought to be limiting factor in the performance of gas sensors.

According to the invention, an ohmic contact is formed of metal 13 on the second face 11b of diamond layer 11, adjacent the highly doped region 11c. The highly doped region preferably produces a contact resistance of less than $10^{-3}$ $\Omega$-cm$^2$. A first and second electrode 14 and 15 respectively, connect the Schottky contact 12 and ohmic contact 13 respectively. Suitable encapsulation 17 is used to protect the device, While allowing gas to interact with the diamond layer 11 at the first face and thereby altering the Schottky barrier height. It will be understood by those having skill in the art that suitable encapsulation 17 may also be provided on Schottky contact 12 for protective purposes, as long as gas interaction is still provided.

Figure 2:
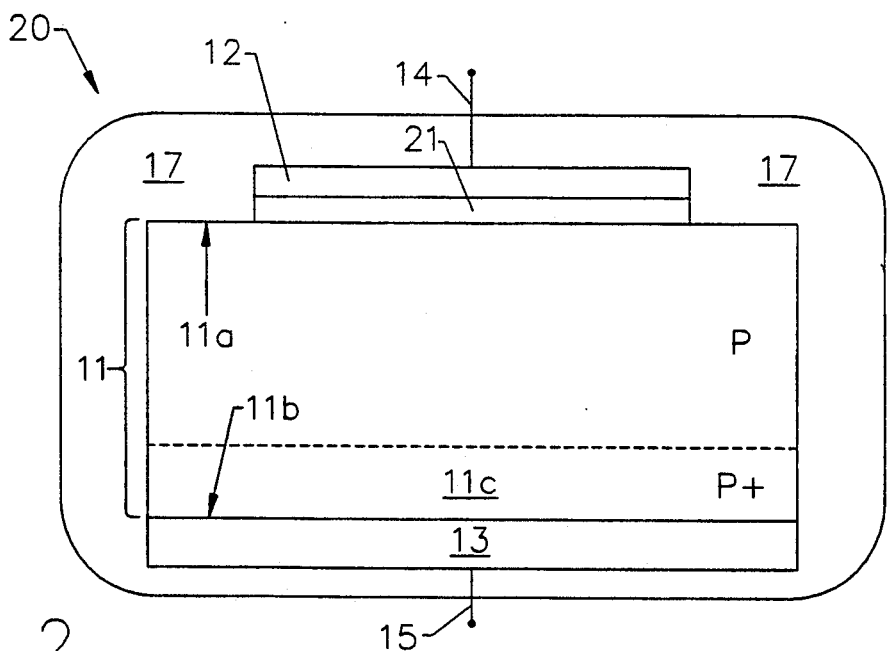
FIG. 2 illustrates a cross-sectional view of a first embodiment of a Schottky diode according to the present invention.

Referring now to FIG. 2, a first embodiment of a Schottky diode 20 according to the invention is shown. This embodiment is similar to the gas sensor 10 shown in FIG. 1, except that the encapsulation 17 prevents penetration of ambient gases into diamond layer 11. Layer 12 is also preferably at least 2000 Å thick.

Figure 3:
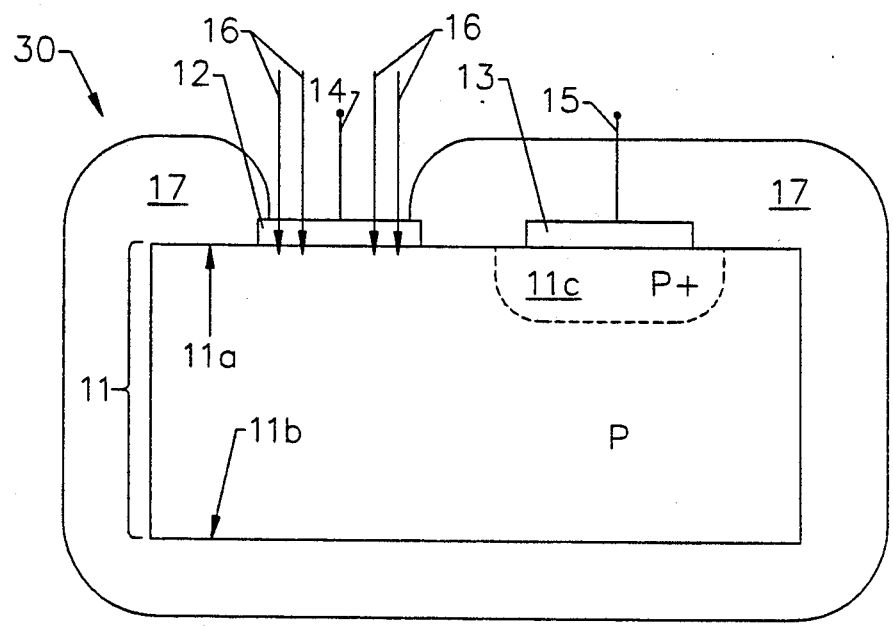
FIG. 3 illustrates a cross-sectional view of a second embodiment of a gas sensor according to the present invention.
Figure 4:
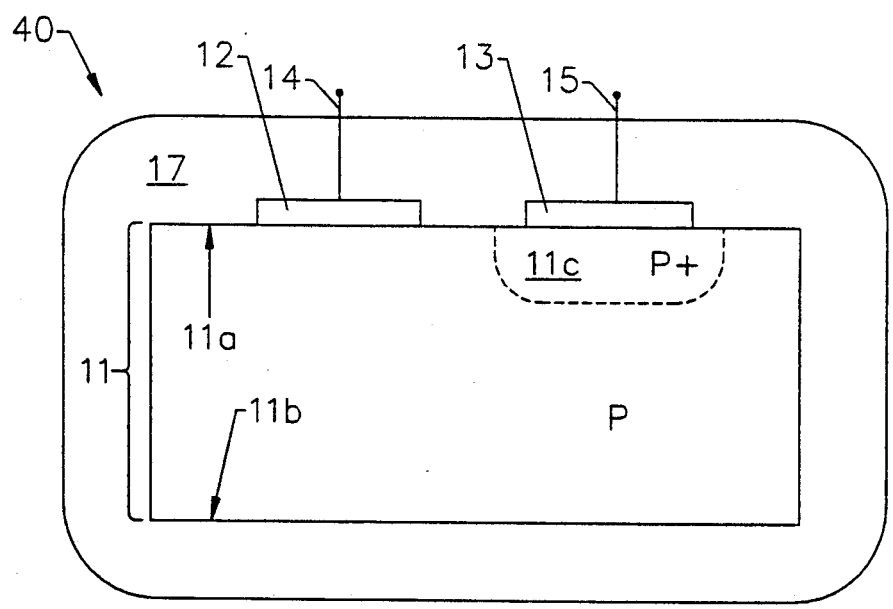
FIG. 4 illustrates a cross-sectional view of a second embodiment of a Schottky diode according to the present invention.

FIG. 3 illustrates a second embodiment of a gas sensor according to the present invention. As shown in FIG. 3, gas sensor 30 includes both an ohmic contact 13 and a Schottky contact 12 on the first face 11a of the diamond layer 11. Accordingly, heavily doped region 11c is formed at first face 11a adjacent ohmic contact 13. FIG. 4 illustrates a second embodiment of a Schottky diode 40 including Schottky contact 12 and ohmic contact 13 at the first face 11a of the diamond substrate. In the embodiments of FIGS. 3 and 4, it is assumed that layer 11 is monocrystalline diamond, so that layer 21 is not shown.

The Schottky diodes and gas sensors of FIGS. 1–4 can be fabricated by using natural (type IIb) diamond crystals 11 which are polished and chemically cleaned in CrO$_3$+H$_2$SO$_4$ acid solution followed by cleaning in aqua regia (3HCl+1HNO$_3$) and RCA solutions. Platinum or palladium films are formed on the first surface 11a of the diamond crystal 11 using a well known resistance heating technique. Region 11c may be formed by ion implanting the second face 11b (FIG. 1 or FIG. 2) or the first face 11a (FIG. 3 or FIG. 4) of diamond layer 11, as appropriate, with boron. The implantation dose is preferably $5\times10^{16}$cm$^{-2}$ at an energy of 60 keV and a target temperature of 200° C. The diamond crystals are then annealed in a furnace at about 1200° C. for 30 minutes at $1\times10^{-7}$Torr. The graphite formed during implantation and annealing is then etched in CrO$_3$+H$_2$SO$_4$ acid solution at about 200° C. A high atomic boron concentration at the appropriate surface 11a (FIG. 1 or FIG. 2) or 11b (FIG. 3 or FIG. 4) of $10^{20}$–$10^{21}$cm$^{-3}$ is obtained.

Then, metal contact 13 is formed using a refractory metal, preferably titanium, about 200 Å to about 400 Å thick. Other refractory metals may also be used. A gold passivating layer, preferably about 1000 Å to about 1500 Å thick may then be formed on the refractory metal layer. Other passivating layers may also be used. An anneal may then be performed at about 800° C. to about 850° C. for a time period of about fifteen minutes to about ninety minutes, to convert at least a portion of the titanium layer to titanium carbide. A low resistance source contact is thereby formed. The process for forming the ohmic contact layer 13 is similar to the process for forming ohmic contacts on diamond as described by Moazed et al. in A Thermally Activated Solid State Reaction Process for Fabricating Ohmic Contacts to Semiconducting Diamond, Applied Physics Journal, Vol. 68, No. 5, September, 1990.

Figure 5:
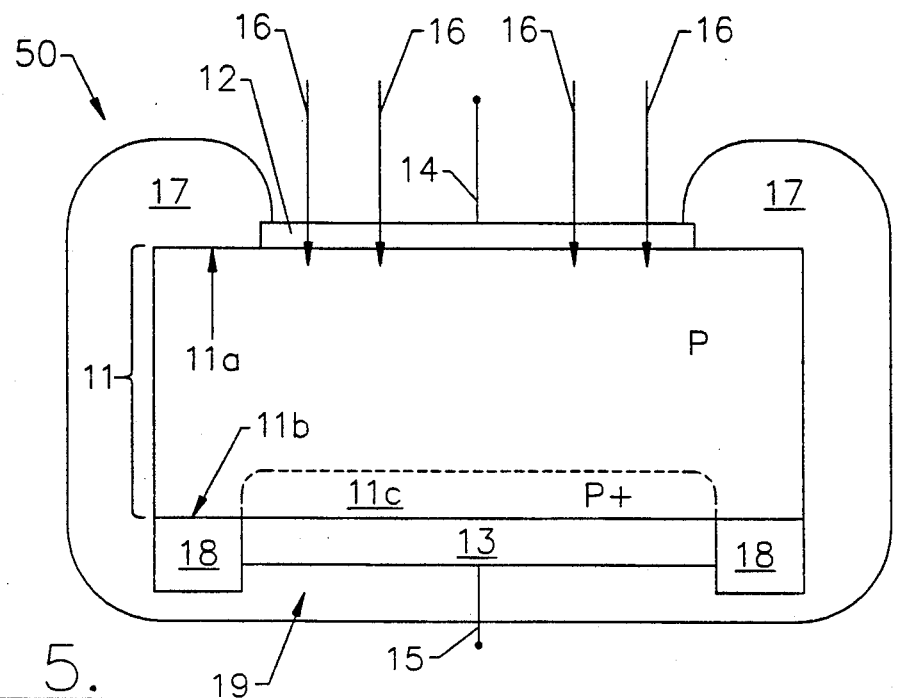
FIG. 5 illustrates a cross-sectional view of a third embodiment of a gas sensor according to the present invention.

Referring now to FIG. 5, a third embodiment of the gas sensor according to the invention is described. Gas sensor 50 is similar to gas sensor 10 described in FIG. 1 except that diamond layer 11 is itself formed on a substrate 18. The substrate 18 may be a diamond substrate or a nondiamond substrate. To facilitate formation of a monocrystalline diamond layer 11, substrate 18 is preferably crystalline silicon carbide, cubic boron nitride, crystalline copper or crystalline nickel. Alternatively, substrate 18 may be a diamond substrate. A polycrystalline diamond layer 11 may also be grown on a nondiamond or diamond substrate using techniques well known to those having skill in the art. If a polycrystalline diamond layer 11 is used, layer 21 is also preferably present, as was described above.

Figure 6:
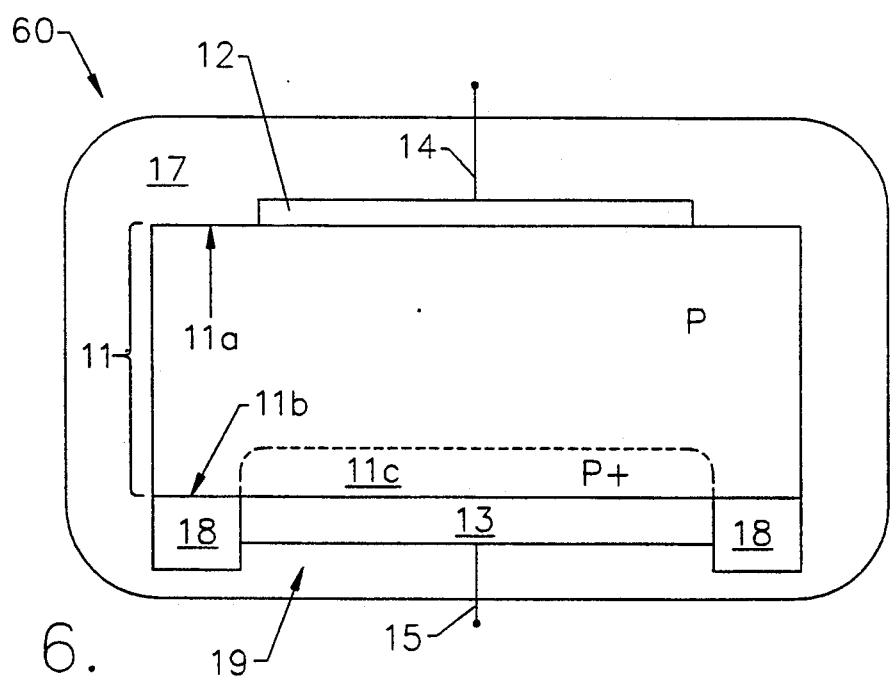
FIG. 6 illustrates a cross-sectional view of a third embodiment of a Schottky diode according to the present invention.

As shown in FIG. 5, a portion of substrate 18 is removed to form an aperture 19 therein about 2 mm in diameter, to allow access to back face 11b of diamond layer 11. A heavily doped boron region 11c is formed by implantation through the aperture 19. An ohmic contact 13 is then formed as Was already described. FIG. 6 illustrates a similar configuration of a Schottky diode 60 having an implanted region 11c on the back face 11b of diamond layer 11.

Figure 7:
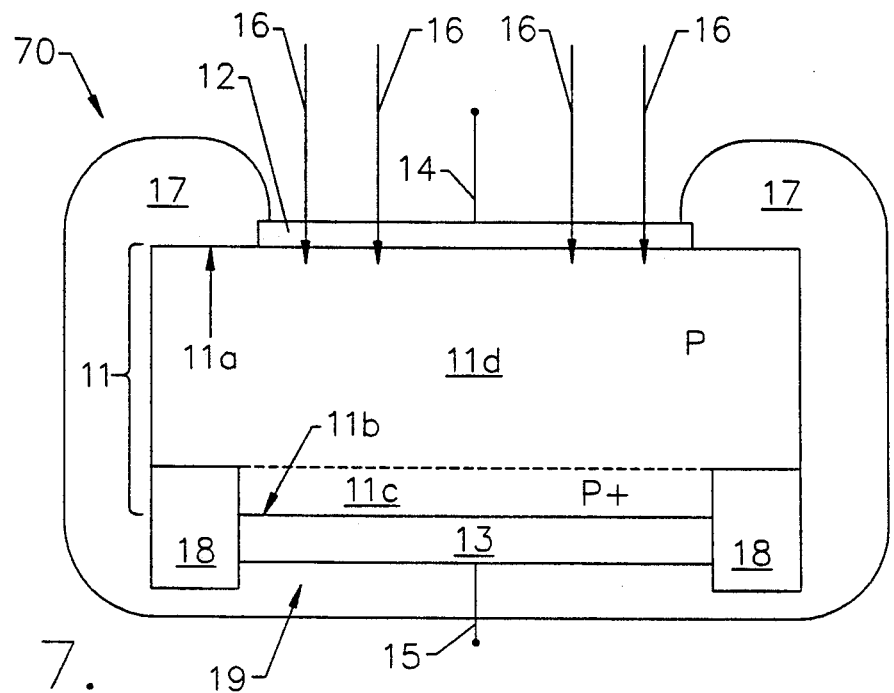
FIG. 7 illustrates a cross-sectional view of a fourth embodiment of a gas sensor according to the present invention.
Figure 8:
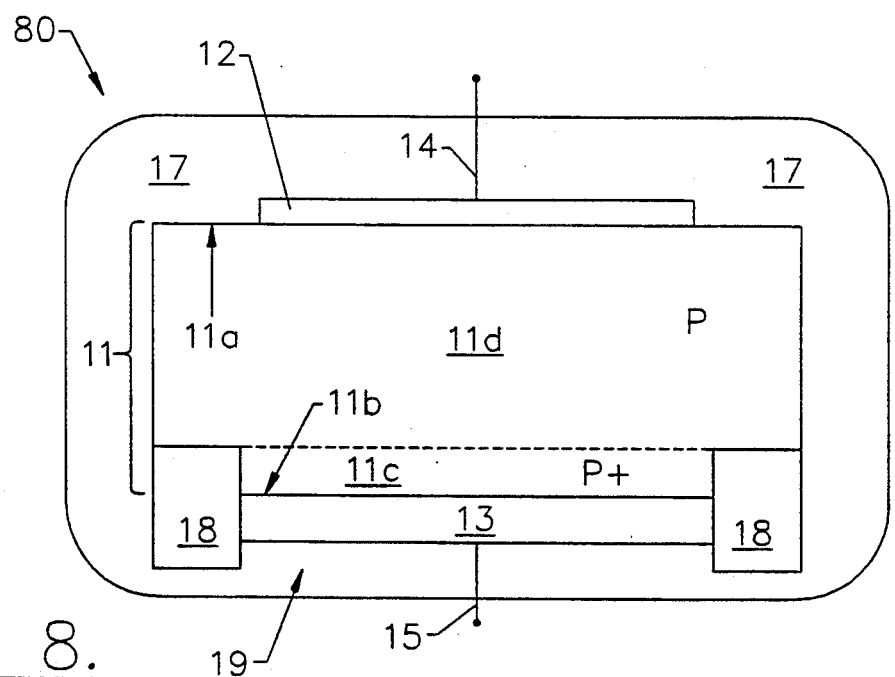
FIG. 8 illustrates a cross-sectional view of a fourth embodiment of a Schottky diode according to the present invention.

Referring now to FIG. 7, yet another embodiment of a diamond based gas sensor 70 according to the present invention is shown. In this embodiment, heavily doped region 11c is grown on lightly doped portion 11d using in situ doping through the aperture 19. An in situ doped region having thickness of between about 0.3 $\mu$m and about 1 $\mu$m is formed. FIG. 8 illustrates a Schottky diode 80 formed using an in situ doped heavily born doped region 11c as described in connection with FIG. 7.

According to the invention, heavily doped boron layer 11c, in combination with contact 13 provides a low resistance ohmic contact. The low resistance ohmic contact dramatically reduces the frequency dependence of the measured capacitance of a diamond Schottky diode and diamond gas sensor. This strong frequency dependence of the measured capacitance was heretofore assumed to result from the inherent properties of the diamond itself, i.e. deep level states and series resistance. According to the invention, by providing a low contact resistance ohmic contact for the Schottky diode and gas sensor, improved device performance may be obtained.

In order to compare the performance of a Schottky diode with and without the ohmic contact of the present invention, natural (type IIb) diamond crystals were polished and chemically cleaned in $CrO_3+H_2SO_4$ acid solution, followed by cleaning in aqua regia ($3HCl+1HNO_3$) and RCA solutions. Aluminum (Al) and Platinum (Pt) films (about 2000 Å in thickness) were deposited on two different cleaned diamond crystals using a resistance heating technique. A molybdenum mask, with 355.6 $\mu$m diameter holes, was used during deposition to define metal dots on the diamond crystals. In order to study the effect of back contact resistance on capacitance/voltage (C-V) characteristics, the backside of some of the crystals were boron (B) ion implanted to achieve a high B concentration region $11c$ at the surface. The implantation conditions were as follows: Dose - $5\times10^{16}$cm$^{-2}$; Energy - 60 keV; Target temperature $-200°$ C. The crystals were then annealed in a furnace at 1200° C. for 30 min at $1\times10^{-7}$Torr. The graphite formed during implantation and annealing was etched in $CrO_3+H_2HO_4$ acid solution at abut 200° C. A high atomic B concentration at the second surface $11b$ of $10^{20}$-$10^{21}$cm$^{-3}$ was obtained.

Electrical measurements were performed on the contacts in a vertical configuration after mounting the samples on a platinum plate using silver paste, with the silver paste contacting region $11b$ (no ohmic contact) or $11c$ (ohmic contact). Current-voltage (I-V) measurements were performed using an HP 4145B semiconductor parameter analyzer. An HP4284A LCR meter was used to perform the C-V measurements. The I-V characteristics of Al and Pt contacts showed excellent rectification. At an applied bias of 20 V, reverse leakage current densities of $4.1\times10^{-8}$ and $6.3\times10^{-9}$ A/cm$^2$ were obtained for Al and Pt contacts, respectively. The C-V measurements were performed in a parallel circuit mode because of the high impedance of metal/diamond Schottky junctions. The reliability of C-V measurements was evaluated by a quality factor Q, expressed as $Q=RC\omega$, where R is the equivalent parallel resistance and $\omega$ is the angular frequency. A value of $Q>5$ was considered to be a reliable measurement.

Figure 9B:
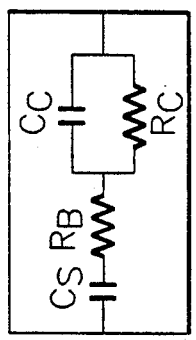
FIGS. 9A–9B illustrate capacitance-voltage measurements of a conventional Schottky diode and an equivalent circuit model for this diode, respectively.
Figure 9A:
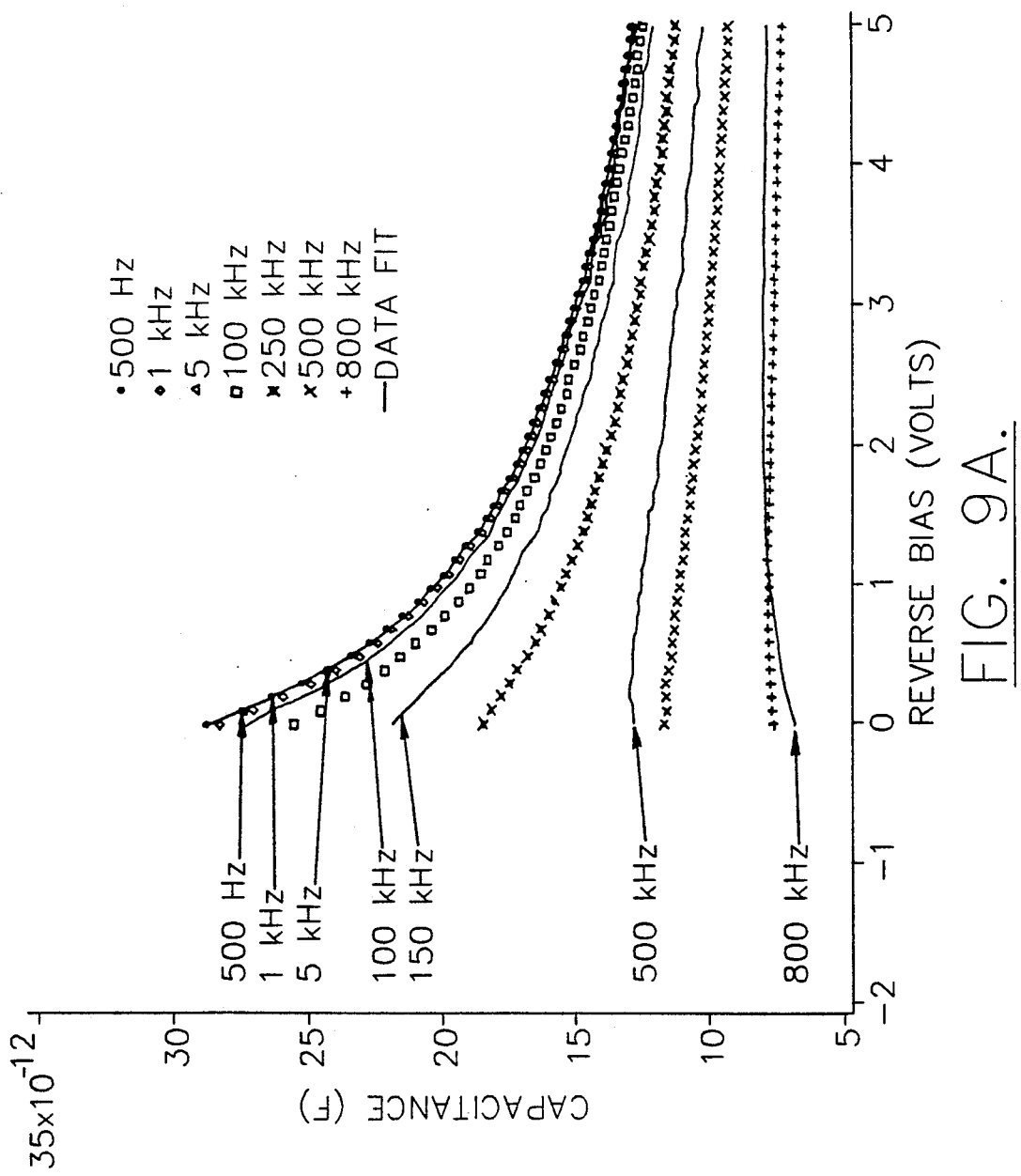
Figure 10B:
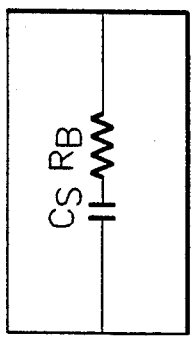
FIGS. 10A–10B illustrate capacitance-voltage measurements of a Schottky diode according to the present invention, and an equivalent circuit model for this diode, respectively.
Figure 10A:
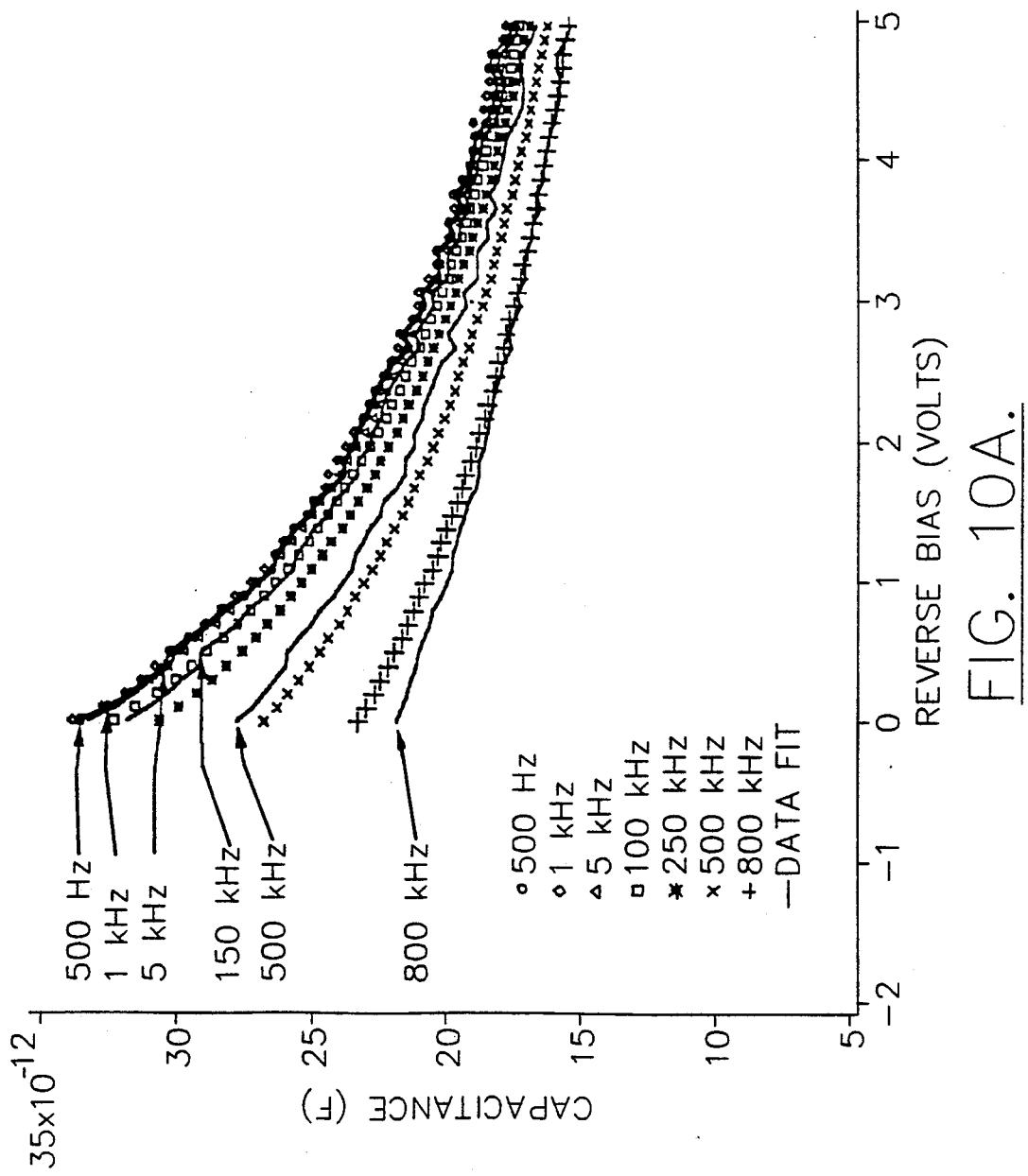

The C-V measurements as a function of frequency (500 Hz to 800 kHz) performed on Al/diamond structure before and after back side implantation are shown in FIGS. 9a and 10a, respectively. The frequency dependence of capacitance observed in FIG. 9a is minimized significantly in FIG. 10a. The heavily doped boron layer $11c$ dramatically reduces the frequency dependence of the C-V curves. Similar C-V curves were obtained for Pt contacts fabricated on another natural diamond before and after back side implantation. Plots of 1/C$^2$ versus reverse bias voltage yielded straight lines for the entire bias and frequency range investigated. A linear least square fit through 1/C$^2$-V for data in FIG. 10a at 500 Hz, yields a value of $2.9\pm0.2\times10^{16}$cm$^{-3}$ for the dopant concentration and a value of $2.1\pm0.1$ eV for the barrier height. The corresponding values for Pt contacts on a similar natural diamond were $2.6\pm0.1\times10^{16}$cm$^{-3}$ and $2.3\pm0.1$ eV.

The value for the dopant concentration is the uncompensated B concentration and is in agreement with other reported values. Secondary ion mass spectrometry (SIMS) analysis of a natural (type IIb) diamond showed an atomic B concentration of $\approx1-5\times10^{16}$cm$^{-3}$. This value agrees well with the ionized dopant concentration in the depletion region (obtained from C-V measurements) of the metal-diamond diodes investigated. Also, the Schottky barrier height is independent of the metal work function. This is believed to be due to Fermi level pinning.

An AC equivalent circuit shown in FIG. 10b has been used to model the C-V measurements shown in FIG. 10a. In this circuit, $C_s$ (F/cm$^2$) is the specific capacitance of the Schottky barrier, $R_B$ is the bulk resistance of diamond, $C_c$ (F/cm$^2$) is the specific contact capacitance and $R_c$ ($\Omega$-cm$^2$) is the specific contact resistance. Measured capacitance, $C_m$ (F) of the device can be expressed as:

$$C_m = G_B A_S C_S \frac{\omega^2 C_C(G_B C_S R_a + G_B C_c + G_C C_S) + G_C(G_C G_B - \omega^2 C_C C_S)}{(G_C G_B - \omega^2 C_C C_S)^2 + \omega^2 (C_C G_B + G_B + C_S R_a G_B + G_C C_S)^2} \quad (1)$$

where, $A_s$ (cm$^2$) is the Schottky contact area, $A_c$(cm$^2$) is the contact area, $G_c$(S/cm$^2$) is the contact specific conductance, $G_B$ (S/cm$^2$) is the bulk specific conductance, $\omega$ is the angular frequency and $R_a=A_s/A_c$. It can be seen from Equation 1 that, for low frequencies $C_m\approx A_s.C_s$. Using this model, fits were made to the C-V data (solid lines), as shown in FIG. 9a. The fit to experimental data is reasonably good for all frequencies in the range 500 Hz to 800 kHz. It was assumed in the model that, $C_c$ and $G_c$ are not a function of voltage and/or frequency. $C_c$ and $G_c$ were measured by performing C-V and I-V measurements, respectively, on Ag/-diamond structures with low resistance back contacts. The following values were used for the variables in the model; $G_B=7.2\times10^{-2}$S/cm$^2$, $G_c=5.1\times10^{-6}$S/cm$^2$, $A_s=9.9\times10^{-4}$cm$^2$, $R_a=4\times10^{-3}$, $C_c=1.8\times10^{-9}$F/cm$^2$. The values of $C_m$ as a function of bias at 500 Hz were assumed to be equal to $C_s$. The value of $G_B$ listed above corresponds to a bulk resistance of 14 k$\Omega$. This value was in good agreement to the measured value of the bulk resistance of natural diamond.

The circuit, shown in FIG 10b can be used to model the frequency dependence of C-V measurements on rectifying contacts to back side implanted diamond crystals according to the present invention. In this case, $C_m$ becomes:

$$C_m=(A_S C_S G_B^2)/(G_B^2+\omega^2 C_S^2) \quad (2)$$

It can be seen from Equation 2 that, for low frequencies, $C_m\approx A_s.C_s$. Using this model, fits (solid lines) were made to the C-V data obtained from measurements on Al contacts with implanted back contact (FIG. 10a). It is observed that the fit to experimental data is reasonably good for all frequencies in the range 500 Hz to 800 kHz. As before, the values of $C_m$ as a function of bias at 500 Hz were assumed to be equal to $C_s$. A value of 0.23 S/cm$^2$ was used for $G_B$ in the model. This corresponds to a value of 4.3 k$\Omega$ for the bulk resistance of diamond.

In summary, differential capacitance-voltage (C-V) measurements were performed on Al and Pt rectifying contacts on natural (type IIb) diamonds. Capacitance-voltage data showed frequency dependence, which decreased significantly after reducing the back contact impedance. Accordingly, the frequency dependence of capacitance-voltage data seems primarily to be an effect of back contact capacitance and resistance, as well as the bulk resistance of diamond. High performance Schottky diodes and gas sensors are obtained.

In the drawings and specification, there have been disclosed typical preferred embodiments of the invention and, although specific terms are employed, they are used in a generic and descriptive sense only and not for purposes of limitation, the scope of the invention being set forth in the following claims.

We claim:

1. A gas sensor comprising:
   a diamond layer having first and second opposing faces;
   a first contact on said first face, wherein said first contact forms a Schottky barrier of predetermined Schottky barrier height between said first contact and said first face, and wherein said first contact allows gas to interact with said first face and alter said predetermined Schottky barrier height; and
   a second contact on said second face, wherein said diamond layer includes a highly doped region adjacent said second contact, said highly doped region being doped at a concentration of at least $10^{20}$ atoms per cubic centimeter, and wherein said second contact forms an ohmic contact with said highly doped region.

2. The gas sensor of claim 1 wherein said highly doped region comprises a region which is doped with boron at a concentration of at least $10^{20}$ atoms per cubic centimeter.

3. The gas sensor of claim 1 wherein said second contact has contact resistance of less than $10^{-3}$ $\Omega$-cm$^2$.

4. The gas sensor of claim 1 wherein said diamond layer is a monocrystalline diamond layer.

5. The gas sensor of claim 1 wherein said diamond layer is a polycrystalline diamond layer, said gas sensor further comprising at least one of a layer of undoped diamond and a thin layer of silicon dioxide, between said second contact and said polycrystalline diamond layer.

6. The gas sensor of claim 1 wherein said first contact comprises a catalytic metal layer which is sufficiently thin to allow gas interaction with said first face.

7. The gas sensor of claim 6 wherein said first contact comprises at least one of a platinum and palladium layer less than about 1000 Ångstroms thick.

8. The gas sensor of claim 1 further comprising at least one of a diamond substrate and a nondiamond substrate on said second face.

9. A gas sensor comprising:
   a diamond layer having first and second opposing faces;
   a first contact on said first face, wherein said first contact forms a Schottky barrier of predetermined Schottky barrier height between said first contact and said first face, and wherein said first contact allows gas to interact with said first face and alter said predetermined Schottky barrier height; and
   a second contact on said second face, wherein said diamond layer includes a doped region adjacent said second contact, and wherein said second contact forms an ohmic contact with said doped region; and
   at least one of a diamond substrate and a nondiamond substrate on said second face, wherein said substrate includes an aperture therein, and wherein said second contact layer is formed on said second face, within said aperture.

10. A gas sensor comprising:
    a diamond layer having a Schottky contact and an ohmic contact thereon, and a highly doped region adjacent said ohmic contact, said highly doped region being doped at a concentration of at least $10^{20}$ atoms per cubic centimeter, said gas sensor being configured such that gas external to said gas sensor is absorbed within said diamond layer, said diamond layer being responsive to gas absorbed therein to alter the barrier height of said Schottky contact and thereby provide a gas sensor.

11. The gas sensor of claim 10 wherein said highly doped region comprises a region which is doped with boron at a concentration of at least $10^{20}$ atoms per cubic centimeter.

12. The gas sensor of claim 10 wherein said ohmic contact has contact resistance of less than $10^{-3}$ $\Omega$-cm$^2$.

13. The gas sensor of claim 10 wherein said diamond layer is at least one of a monocrystalline diamond layer and a polycrystalline diamond layer.

14. The gas sensor of claim 10 wherein said diamond layer is a polycrystalline diamond layer, said gas sensor further comprising at least one of a layer of undoped diamond and a thin layer of silicon dioxide, between said ohmic contact and said polycrystalline diamond layer.

15. The gas sensor of claim 10 wherein said Schottky contact comprises a catalytic metal layer which is sufficiently thin to allow gas interaction with said diamond layer.

16. The gas sensor of claim 15 wherein said Schottky contact comprises at least one of a platinum and palladium layer less than about 1000 Ångstroms thick.

17. The gas sensor of claim 10 further comprising at least one of a diamond substrate and a nondiamond substrate on said diamond layer.

18. A gas sensor comprising:
    a diamond layer having a Schottky contact and an ohmic contact thereon, and a doped region adjacent said ohmic contact, said diamond layer being responsive to gas absorbed therein to alter the barrier height of said Schottky contact;
    at least one of a diamond substrate and a nondiamond substrate on said diamond layer, wherein said substrate includes an aperture therein, and wherein said ohmic contact layer is formed on said diamond layer, within said aperture.

19. A diode comprising:
    a diamond layer having a Schottky contact and an ohmic contact thereon, and a highly doped region adjacent said ohmic contact said highly doped region being doped at a concentration which is greater than $10^{20}$ atoms per cubic centimeter, to thereby provide a Schottky diode.

20. The diode of claim 19 wherein said highly doped region comprises a region which is doped with boron at a concentration of at least $10^{20}$ atoms per cubic centimeter.

21. The diode of claim 19 wherein said ohmic contact has a contact resistance of less than $10^{-3}$ $\Omega$-cm$^2$.

22. The diode of claim 19 wherein said diamond layer is a monocrystalline diamond layer.

23. The diode of claim 19 wherein said diamond layer is a polycrystalline diamond layer, said diode further comprising at least one of a layer of undoped diamond and a thin layer of silicon dioxide, between said ohmic contact and said polycrystalline diamond layer.

24. The diode of claim 19 wherein said Schottky contact comprises a metal layer more than about 2000 Ångstroms thick.

25. The diode of claim 19 further comprising at least one of a diamond substrate and a nondiamond substrate on said diamond layer.

26. A diode comprising:

a diamond layer having a Schottky contact and an ohmic contact thereon, and a highly doped region adjacent said ohmic contact, to thereby provide a Schottky diode; and at least one of a diamond substrate and a nondiamond substrate on said diamond layer wherein said substrate includes an aperture therein, and wherein said ohmic contact layer is formed on said diamond layer, within said aperture.

* * * * *